(12) United States Patent
Bönsch et al.

(10) Patent No.: US 9,353,036 B1
(45) Date of Patent: May 31, 2016

(54) PROCESS FOR PRODUCING FATTY ALCOHOLS FROM FATTY ACID METHYL ESTER

(71) Applicant: L'Air Liquide, Societe Anonyme pour l'Etude et l'Exploitation des Procedes Georges Claude, Paris (FR)

(72) Inventors: Rudolf Bönsch, Nackenheim (DE); Ingo Bauer, Bad Vilbel (DE)

(73) Assignee: L'Air Liquide Société Anonyme Pour L'Étude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 14/898,613

(22) PCT Filed: Jun. 17, 2014

(86) PCT No.: PCT/EP2014/062712
§ 371 (c)(1),
(2) Date: Dec. 15, 2015

(87) PCT Pub. No.: WO2014/202601
PCT Pub. Date: Dec. 24, 2014

(30) Foreign Application Priority Data

Jun. 19, 2013 (DE) .................. 10 2013 106 382

(51) Int. Cl.
*C07C 29/128* (2006.01)
*C07C 29/149* (2006.01)
*C07C 31/125* (2006.01)
*C07C 29/80* (2006.01)
*B01J 21/10* (2006.01)

(52) U.S. Cl.
CPC ............... *C07C 29/149* (2013.01); *B01J 21/10* (2013.01); *C07C 29/128* (2013.01); *C07C 29/80* (2013.01); *C07C 31/125* (2013.01)

(58) Field of Classification Search
CPC .... C07C 29/128; C07C 24/149; C07C 31/125
USPC .................................................. 568/877, 885
See application file for complete search history.

(56) References Cited

FOREIGN PATENT DOCUMENTS

| DE | 10 2007 033636 | 1/2009 |
| DE | 10 2007 061872 | 6/2009 |
| EP | 0 454 720 | 11/1991 |
| WO | WO 2013 072664 | 5/2013 |

OTHER PUBLICATIONS

International Search Report for PCT/EP2014/062712, mailed Nov. 3, 2014.

*Primary Examiner* — Elvis O Price
(74) *Attorney, Agent, or Firm* — Justin K. Murray

(57) ABSTRACT

Subject-matter of the invention is a process for producing fatty alcohols by catalytic hydrogenation of fatty acid methyl ester (FAME), in which the FAME initially is hydrogenated to fatty alcohol (FA). The fractions of non-converted FAME remaining in the hydrogenation product are converted to wax ester and methanol in a succeeding transesterification step with FA. According to the invention, catalysts on the basis of magnesium oxide or hydrotalcite are used. After separating the methanol and the FA as target product, a stream enriched in wax ester is recirculated to the hydrogenation reactor.

4 Claims, 2 Drawing Sheets

PROCESS FOR PRODUCING FATTY ALCOHOLS FROM FATTY ACID METHYL ESTER

CROSS REFERENCE TO RELATED APPLICATIONS

This application is a §371 of International PCT Application PCT/EP2014/062712, filed Jun. 17, 2014, which claims the benefit of DE 10 2013 106 382.9, filed Jun. 19, 2013, both of which are herein incorporated by reference in their entireties.

FIELD OF THE INVENTION

Embodiments of the invention relate to a process for obtaining fatty alcohols by catalytic hydrogenation of fatty acid methyl ester. In particular, embodiments of the invention relate to the use of novel catalysts for the production of fatty alcohols, wherein as compared to the production methods known from the prior art less undesired by-products are obtained.

BACKGROUND

According to the prior art, the production of biodegradable fatty alcohols as raw material for example for the detergent industry is effected either by catalytic hydrogenation of breakdown fatty acids in a discontinuously operated reactor with catalyst slurry or continuously in a trickle-bed reactor with solid catalyst bed on the basis of methyl esters or wax esters of the corresponding fatty acids.

In the production of fatty alcohols by hydrogenation of methyl esters, fractions of non-converted methyl ester still are present in the produced fatty alcohol. During the hydrogenation, the throughput through the shaft or tubular reactor therefore already is adjusted such that only traces of methyl ester can be found in the exiting product stream, which ultimately limits the maximum possible throughput at the reactor. This procedure is necessary, since methyl esters of a certain C chain length n form azeotropes with the associated alcohols of the C chain length n−1, and the remaining methyl esters in the fatty alcohol mixture therefore cannot be separated completely by distillation.

In the patent EP 0 454 720 B1 of Davy McKee Ltd. a process is described, with which a large amount of the fatty alcohol can be recovered from a mixture of fatty alcohols (FA) and fatty acid methyl esters (ME). For this purpose, the FA/ME mixture initially is mixed with a homogeneous catalyst, preferably an alkyl titanate, and a transesterification of the ME to wax esters (WE) and methanol (MeOH) is carried out. After reaching the chemical equilibrium, the product mixture which now contains FA, WE, MeOH and small traces of ME is liberated from MeOH by distillation. The residue of FA, WE and small traces of ME obtained by distillation subsequently is liberated from a large amount of the contained FA in a further distillation. The residue of the second distillation now is again mixed with MeOH and subjected to a second transesterification, in which FA and ME again are obtained from the contained WE together with MeOH. The used excess of MeOH is separated from the obtained reaction product by evaporation, and the latter is fractionated in a further distillation into a distillate comprising FA and ME as well as a distillation residue, which also contains the homogeneous catalyst used in the first step and is partly recirculated and partly disposed of. Thus, two reaction and four fractionation steps must be carried out in this process.

The unexamined German application DE 10 2007 033 636 A1 describes a production process for fatty alcohols by hydrogenation of fatty acid methyl esters and the separation of the fatty alcohol mixtures thus produced into individual fractions after the hydrogenation by distillation. In particular, there is taught a process for separating a lower alkyl ester of a fatty acid from a fatty alcohol fraction or from a fatty alcohol mixture. This object is solved in that the fatty alcohol fraction or the fatty alcohol mixture is transesterified to fatty alcohol (FA), wax ester (WE) and the lower alkyl alcohol and at the same time the lower alkyl alcohol is discharged from the reaction mixture substantially completely and the wax ester is separated from the obtained product. In particular, it is proposed to carry out the transesterification in the presence of a heterogeneous transesterification catalyst. In contrast to the homogeneous catalyst which is used in the process according to EP 0 454 720 B1, there is not obtained a catalyst-containing residue. The wax ester obtained is pure and free from catalyst and therefore can be recirculated to the hydrogenation of fatty acid alkyl ester without further purification or processing. In DE 10 2007 033 636 A1, there was preferably used a titanium silicalite catalyst.

SUMMARY OF THE INVENTION

Our own experiments have shown that the use of acidic catalysts on the basis of titanium silicalite leads to the formation of undesired by-products during the transesterification. These are high-boiling, still unidentified products which cannot be separated from the wax esters by distillation. It is assumed that these are di-fatty alcohol ethers. Furthermore, when carrying out the transesterification in the presence of catalysts on the basis of titanium silicate, olefins also were observed as disturbing by-products.

Therefore, it is the object underlying embodiments of the present invention to indicate a rather simple process for obtaining fatty alcohols (FA) from fatty acid methyl ester (FAME), in which by-products as described above do not occur or only to a small extent.

The object is solved by a process according to the embodiments disclosed herein. In one embodiment, the following process steps are carried out in detail:

(a) supplying a feed stream containing fatty acid methyl ester to a hydrogenation stage, conversion of the feed stream in the presence of hydrogen under hydrogenation conditions on a bed of solid, granular hydrogenation catalyst, discharging a first material stream containing fatty alcohol, methanol and non-converted FAME, (b) supplying the first material stream to a distillation stage, separating the methanol as top product of the distillation, and discharging the bottom product of the distillation as second material stream comprising fatty alcohol and FAME, (c) supplying the second material stream to a transesterification reactor filled with a bed of solid, granular catalyst, transesterification of the second material stream under transesterification conditions to a third material stream comprising fatty alcohol and wax ester (WE) in counterflow with an inert gas stream as stripping gas stream, wherein the methanol produced during the transesterification is separated with the stripping gas as top product and the third material stream comprising fatty alcohol and wax ester is discharged, (d) supplying the third material stream to a separation stage operating by a thermal separation process, separating a fourth material stream enriched in wax ester, discharging a fifth material stream depleted of wax ester and enriched in fatty alcohol as fatty alcohol product stream, (e) recirculating the fourth material stream enriched in wax ester to the hydrogenation stage (a), wherein the process according to the invention is characterized in that in process step (c) a transesterification catalyst on the basis of magnesium oxide or hydrotalcite is used.

Further advantageous aspects of the invention can be found in the dependent claims.

Hydrogenation conditions or transesterification conditions are understood to be reaction conditions which effect at least a partial conversion, preferably an extensive conversion of the FAME to fatty alcohol or to wax ester. The conversion conditions required for the hydrogenation or transesterification, in particular suitable reaction temperatures, pressures and space velocities, are known in principle to the skilled person from the prior art, for example from the documents discussed above. Necessary adaptations of these conditions to the respective operating requirements, for example to the composition of the feed stream or to the type of catalysts used, will be made on the basis of routine experiments. Conversion conditions particularly suitable in connection with the process according to the invention will be disclosed in the following exemplary embodiment.

Wax ester is understood to be the product of the esterification of the obtained fatty alcohols with the corresponding fatty acids.

As stripping gas stream, there can be used any gas which shows an inert behavior with respect to the components present in process step (c). For this purpose, nitrogen preferably is used.

Surprisingly, it has been found that when carrying out the transesterification process by using a basic catalyst on the basis of magnesium oxide or hydrotalcite, the above-mentioned impurities resulting from by-products such as olefins and probably di-fatty alcohol ethers only are observed in a very low concentration or even are not detectable, wherein the FAME conversion to wax ester is at least just as good as, in part even better than with the titanium-silicate-based catalysts used according to the prior art.

BRIEF DESCRIPTION OF THE DRAWINGS

Further developments, advantages and possible applications of the invention can also be taken from the following description of an exemplary embodiment and the drawings. All features described and/or illustrated form the invention per se or in any combination, independent of their inclusion in the claims or their back-reference.

DETAILED DESCRIPTION OF THE INVENTION

A preferred aspect of the invention provides that the separation stage in process step (d) is designed as distillation stage, wherein the fourth material stream enriched in wax ester is obtained as bottom product and the fifth material stream depleted of wax ester and enriched in fatty alcohol is obtained as top product. In this way, the target product fatty alcohol can be obtained in high purity.

In an alternative aspect, the thermal separation stage in process step (d) can be designed as winterization stage. The fourth material stream depleted of wax ester, which then has been deposited under winterization conditions, can be separated by means of a mechanical separation process. Winterization is understood to be the cooling of a material stream to below the crystallization temperature of the wax ester, wherein the latter is deposited in solid form. Due to the great difference in the melting points of fatty alcohol and wax ester, a particularly easy and efficient separation is possible in this way. In contrast to other thermal separation processes like the distillation, the products are not subjected to a thermal load. This is advantageous in particular when separating wax esters whose fatty alcohol or fatty acid component is thermally unstable. It is particularly advantageous when the sedimentation, decantation, filtration or combinations thereof are used as mechanical separation process.

Figure 1:
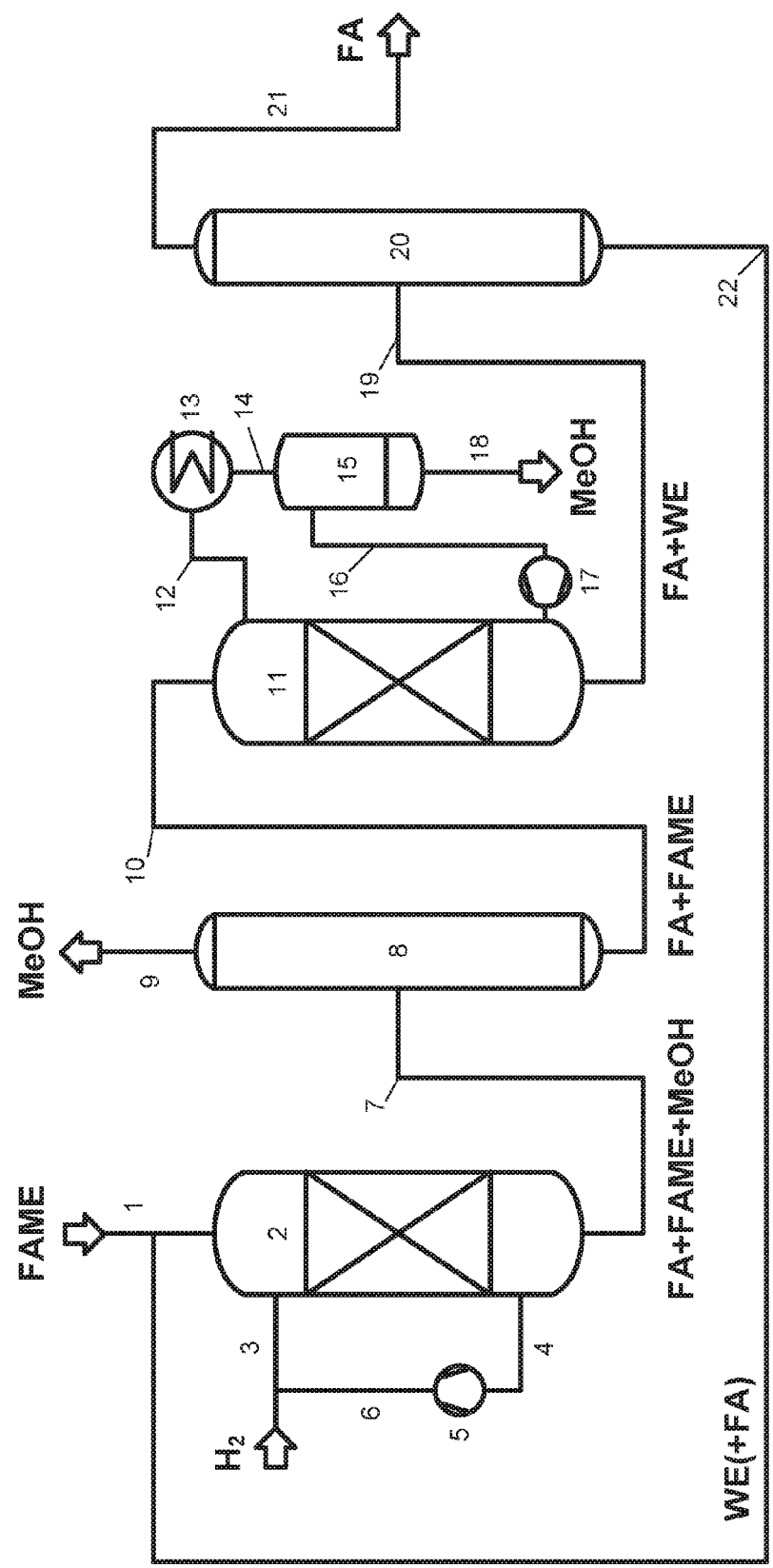
FIG. 1 shows a process of the invention according to a first embodiment.

FIG. 1 shows a schematically represented basic flow diagram of one aspect of the process according to the invention, which will be explained in detail below.

Via conduit 1, a liquid educt stream which contains fatty acid methyl ester (FAME) is supplied to the hydrogenation reactor 2. The hydrogenation reactor contains a bed of a commercially available hydrogenation catalyst in tablet form. Via conduit 3, hydrogen furthermore is supplied to the top of the hydrogenation reactor. The conversion is effected in the hydrogenation reactor in the trickle bed. Non-converted hydrogen is separated at the outlet of the hydrogenation reactor by means of a separating device not shown in the Figure and via conduits 4, 6 and 3 and the compressor 5 recirculated to the top of the hydrogenation reactor. During the hydrogenation, the FAME space velocity typically is between 0.1 to 5 $l/(l_{cat} h)$, preferably 0.5 to 1.5 $l/(l_{cat} h)$, particularly preferably 0.75 $l/(l_{cat} h)$. The temperature typically is between 100 and 300° C., preferably between 120 and 250° C., particularly preferably 180° C. The hydrogen pressure preferably is 50 to 300 bar, absolute, preferably either 50 to 75 bar, absolute, or alternatively roughly 250 bar, absolute (high-pressure hydrogenation).

At the lower end of the hydrogenation reactor a liquid material stream is discharged, which beside non-converted FAME also contains the hydrogenation products fatty alcohol (FA) and methanol. Via conduit 7, this substance mixture is supplied to the distillation column 8. As top product of the distillation column 8 methanol is withdrawn via conduit 9 and supplied to the disposal, processing or direct reuse, for example for the production of FAME. As bottom product of the distillation column 8 a liquid material stream is discharged via conduit 10, which substantially contains FA and FAME. This material stream is charged to the top of the transesterification reactor 11 which is filled with a bed of coarsely porous magnesium oxide granules with a grain size of 2 to 3 mm as transesterification catalyst. The transesterification in turn is carried out in the trickle bed at a temperature of 100 to 300° C., preferably 150 to 250° C., particularly preferably 240° C. and at a pressure of 0.1 to 5 bar, absolute, preferably 0.5 to 2 bar, absolute, particularly preferably at 1 bar, absolute, and at a space velocity of the liquid phase of 0.1 to 5 $l/(l_{cat} h)$, preferably 0.5 to 2 $l/(l_{cat} h)$, particularly preferably 0.75 to 1 $l/(l_{cat} h)$. In counterflow to the liquid phase, nitrogen gas is passed through the transesterification reactor with a space velocity of 2 to 3 $l/(l_{cat} h)$. During the transesterification, FAME is reacted with excess fatty alcohol to obtain wax ester (WE), wherein methanol is released.

At the top of the transesterification reactor, a nitrogen stream loaded with methanol is withdrawn via conduit 12, which in the cooler 13 is cooled to below the dew point of methanol. Via conduit 14, the two-phase mixture gas/liquid is supplied to the separator 15, at the top of which a nitrogen stream liberated from methanol is withdrawn and via conduit 16 and condenser 17 charged to the bottom side of the transesterification reactor 11. Via conduit 18, a further fraction of methanol is withdrawn and supplied to the disposal, processing or direct reuse, for example for the production of FAME.

At the lower end of the transesterification reactor 11 a liquid material stream is discharged, which substantially consists of fatty alcohol (FA) and wax ester (WE). Via conduit 19, the same is charged to a distillation column 20. As top product of the distillation column 20 a material stream containing the target product fatty alcohol is discharged via conduit 21 and supplied to the further processing or direct further use.

As bottom product of the distillation column 20 a liquid material stream is discharged via conduit 22, which substantially contains wax ester beside traces of FA. This material stream is recirculated to the hydrogenation reactor 2 via conduit 22 and again charged at the top of the reactor.

Figure 2:
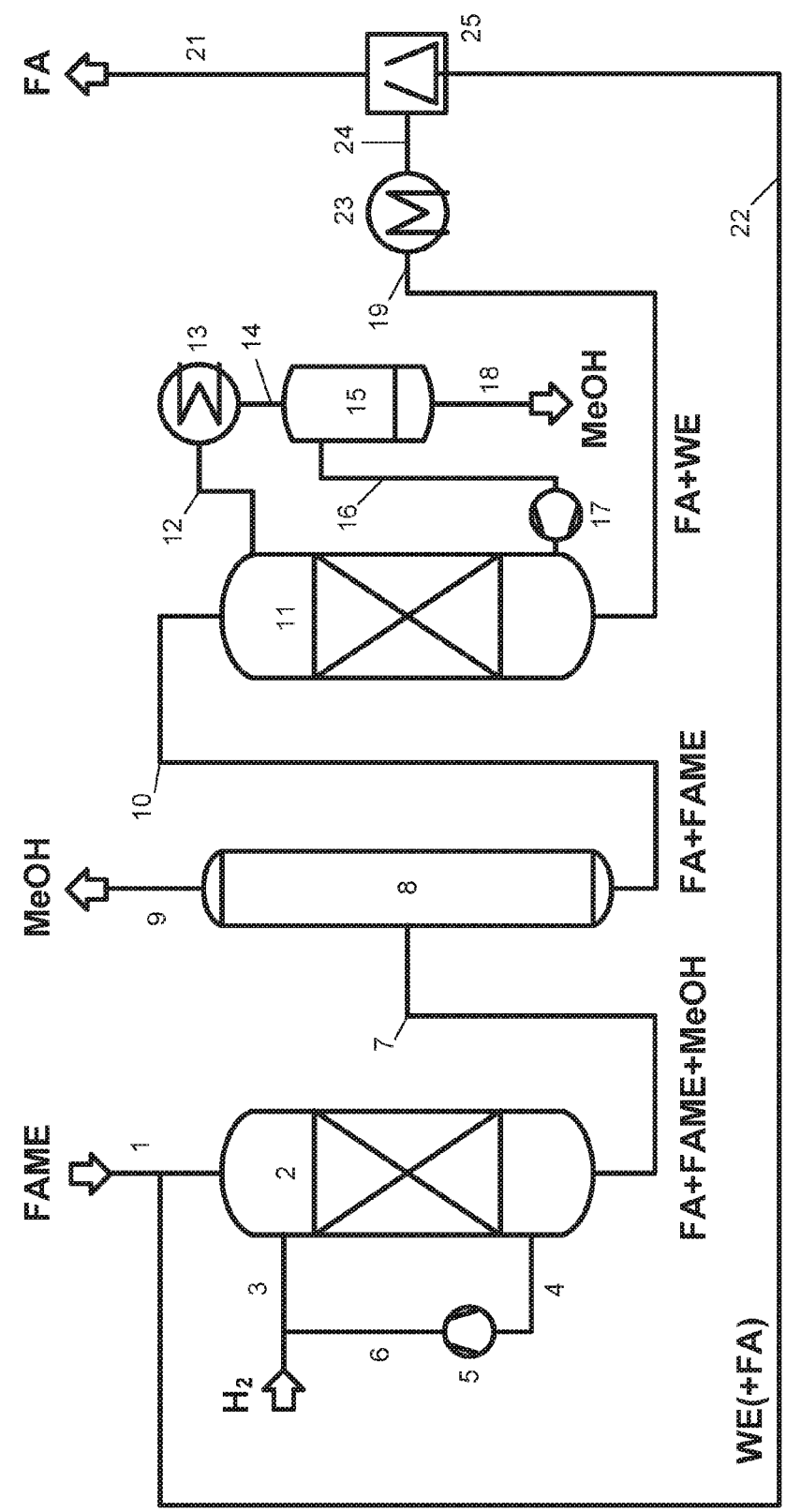
FIG. 2 shows a process of the invention according to a second embodiment.

FIG. 2 shows a schematically represented basic flow diagram of a further aspect of the process according to the invention. The material stream substantially containing FAME and wax ester, which is discharged from the transesterification reactor 11 via conduit 19, is supplied to a cooler 23 via conduit 19 and cooled there to below the crystallization temperature of the wax ester. This procedure also is referred to as winterization. The resulting two-phase mixture of solid wax ester and liquid fatty alcohol subsequently is charged to a centrifuge 25 via conduit 24. The clear supernatant obtained during the centrifugation contains the target product fatty alcohol already in high purity and is supplied to the further processing or direct further use. Beside wax ester as main constituent the crystal mash obtained during the centrifugation also contains fatty alcohol. This material stream is recirculated to the hydrogenation reactor 2 via conduit 22 and again charged at the top of the reactor. The possibly required additional process steps, for example the redissolution of the wax ester to a pumpable solution, are not represented in FIG. 2, but are well-known to the skilled person.

NUMERICAL EXAMPLE

In the following Table, the results of transesterification experiments by using various titanium silicate catalysts, as they were described in the prior art (comparative experiments), are compared with the test results obtained when using magnesium oxide granules (invention). All transesterification experiments were carried out in the trickle bed in a tubular reactor filled with a bed of the respective catalyst, wherein a nitrogen stream constant in all cases was countercurrently passed through the reactor. The composition of the feed mixture each was 95 wt-% of fatty alcohol +5 wt-% of methyl ester. The reactor temperature each was 240° C., the space velocity LHSV constantly was 1 l/($l_{cat}$ h). All experiments were carried out at ambient pressure.

TABLE

Results of the transesterification experiments with titanium silicate catalysts (comparative experiments) and magnesium oxide catalyst (invention)

| | | Products/GC area percentage | | | | |
|---|---|---|---|---|---|---|
| | Catalyst | FA | FAME | WE | Olefins | X [#] |
| Comp. experiment 1 | Ti-silicate 1 | 90 | 3 | 2 | 4 | 1 |
| Comp. experiment 2 | Ti-silicate 2 | 93 | 0 | 5 | 2 | 0 |
| Comp. experiment 3 | Ti-silicate 3 | 94 | 0 | 1 | 1 | 4 |
| Comp. experiment 4 | Ti-silicate 4 | 93 | 2 | 3 | 0 | 2 |
| Comp. experiment 5 | Ti-silicate 5 | 91 | 4.5 | 0.5 | 1 | 3 |
| Comp. experiment 6 | Ti-silicate 6 | 93 | 4 | 1 | 1 | 1 |
| Invention | MgO | 95 | 0 | 5 | 0 | 0 |

[#] X: probably di-FA ether

As can distinctly be seen with reference to the test results shown in the Table, a quantitative conversion of FAME to wax ester is effected in the transesterification process according to the invention by using magnesium oxide granules as catalyst, without disturbing impurities being produced. When using titanium-silicate catalysts according to the prior art, a less quantitative conversion to wax ester and the formation of impurities (olefins and/or component X) is observed under the same reaction conditions.

INDUSTRIAL APPLICABILITY

The invention provides a process with which fatty alcohols can be obtained in high purity as highly desired base chemicals. The catalysts are commercially available and therefore easy to obtain. The hydrogenation catalyst can be exploited better than in the processes known from the prior art; the catalyst costs per ton of produced fatty alcohol thereby are reduced. Furthermore, the process according to the invention leads to an increase of the product yield by better utilization of raw materials.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a non-exclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

LIST OF REFERENCE NUMERALS

[1] conduit
[2] hydrogenation reactor
[3] conduit
[4] heat exchanger
[5] compressor
[6] conduit
[8] distillation column
[9] conduit
[10] conduit
[11] transesterification reactor
[12] conduit
[13] cooler
[14] conduit
[15] conduit
[16] conduit
[17] condenser
[18] conduit
[19] conduit
[20] distillation column
[21] conduit
[22] conduit
[23] cooler
[24] conduit
[25] centrifuge

The invention claimed is:

1. A process for obtaining fatty alcohols (FA) from fatty acid methyl ester (FAME), the process comprising the steps of:
   (a) supplying a feed stream containing fatty acid methyl ester to a hydrogenation stage, conversion of the feed stream in the presence of hydrogen under hydrogenation conditions on a bed of solid, granular hydrogenation catalyst, discharging a first material stream containing fatty alcohol, methanol and non-converted FAME;
   (b) supplying the first material stream to a distillation stage, separating the methanol as top product of the distillation, and discharging the bottom product of the distillation as second material stream comprising fatty alcohol and FAME;
   (c) supplying the second material stream to a transesterification reactor filled with a bed of solid, granular catalyst, transesterification of the second material stream under transesterification conditions to a third material stream comprising fatty alcohol and wax ester (WE) in counterflow with an inert gas stream as stripping gas stream, wherein the methanol produced during the transesterification is separated with the stripping gas as top product and the third material stream comprising fatty alcohol and wax ester is discharged;
   (d) supplying the third material stream to a separation stage operating by a thermal separation process, separating a fourth material stream enriched in wax ester, discharging a fifth material stream depleted of wax ester and enriched in fatty alcohol as fatty alcohol product stream; and
   (e) recirculating the fourth material stream enriched in wax ester to the hydrogenation stage (a),
   wherein in process step (c) a transesterification catalyst on the basis of magnesium oxide or hydrotalcite is used.

2. The process according to claim 1, wherein the separation stage in process step (d) is designed as distillation stage, wherein the fourth material stream enriched in wax ester is obtained as bottom product and the fifth material stream depleted of wax ester and enriched in fatty alcohol is obtained as top product.

3. The process according to claim 1, wherein the separation stage in process step (d) is designed as winterization stage and the fourth material stream enriched in wax ester, which is deposited under winterization conditions, is separated by means of a mechanical separation process.

4. The process according to claim 3, wherein the mechanical separation process is selected from the group consisting of sedimentation, decantation, filtration, and combinations thereof.

* * * * *